United States Patent [19]

Hounsfield

[11] 4,053,781

[45] Oct. 11, 1977

[54] PACKING MEMBER FOR RADIOGRAPHIC POSITIONING MEANS

[75] Inventor: Godfrey Newbold Hounsfield, Newark, England

[73] Assignee: E M I Limited, Hayes, England

[21] Appl. No.: 644,160

[22] Filed: Dec. 24, 1975

[30] Foreign Application Priority Data

Jan. 16, 1975 United Kingdom ................ 1880/75

[51] Int. Cl.$^2$ .......................... A61B 6/02; A61B 6/04
[52] U.S. Cl. ................................ 250/456; 250/445 T
[58] Field of Search .................. 250/445 T, 503, 456, 250/451, 510; 252/478

[56] References Cited

U.S. PATENT DOCUMENTS

| 3,715,587 | 2/1973 | Burkhalter | 250/456 |
| 3,881,110 | 4/1975 | Hounsfield et al. | 250/456 |

OTHER PUBLICATIONS

Classification Definitions, United States Patent Office, June 1962, pp. 250-30.

Primary Examiner—Alfred E. Smith
Assistant Examiner—T. N. Grigsby
Attorney, Agent, or Firm—Fleit & Jacobson

[57] ABSTRACT

In an apparatus for examining a body by means of penetrating radiation a flexible member, containing material, having an absorption to the radiation similar to that of human tissue, is placed in a bag in contact with the body to provide support therefore. The absorbing material may be a viscous material or may be a particulate material which behaves substantially in a viscous manner.

10 Claims, 4 Drawing Figures

PACKING MEMBER FOR RADIOGRAPHIC POSITIONING MEANS

This invention relates to apparatus for examining a body by means of penetrating radiation, such as X-radiation, and it relates especially to means for locating a body in such apparatus.

In our British patent specification No. 1283915, apparatus is described which is capable of examining thin planar slices of the human body by means of penetrating radiation, and for constructing representations of the variation of the absorption or transmission of elements of the body across these slices, with respect to the radiation.

Apparatus according to the aforesaid British patent specification is particularly effective in examining the human head. To achieve an accurate representation of absorption it is necessary to position the head accurately in relation to a source of radiation and a means for detecting the radiation after passage through the body. Suitable accuracy of positioning is obtained by supporting the head in a pouched, flexible member forming one wall of a water reservoir. When the reservoir is filled with water the flexible member holds the head firmly but gently. The source of radiation and the detecting means are scanned relative to the supported head, the scanning movements including a step by step rotation of the source of radiation and detecting means. The water reservoir, apart from its flexible wall, participates in this rotation, and the reservoir in addition to its function of supporting the head, acts as an attenuator serving in all angular positions to compensate substantially for variation in the path length for the radiation across the width of the head.

In our U.S. Pat. No. 3,937,963 a development of the apparatus, more suitable for examining other parts of the body, is described. In that application there is described a means for locating the body comprising a pair of semi-circular members, secured at two points to form a ring. The part of the body to be examined is first surrounded by a tubular, flexible bag, placed in the lower semicircular member and the upper member is attached to form the said ring, surrounding the body and the bag. The bag is then inflated with water until it fits firmly between the body and the ring. The water filled bag thus ensures that the body is held firmly but gently by the locating ring and, by excluding air pockets between the body and the ring, ensures that all regions of the said slice, lying within the locating ring, have an absorption to the radiation substantially the same as that of the body. Other means are provided to compensate for variations in the path length for the radiation across the width of the locating ring. Thus the X-ray absorption across the ring and those compensating means is substantially constant for all radiation paths.

The locating ring and water bag arrangement described in the aforementioned United States Patent can be adapted for use with X-ray apparatus other than that described therein, and for the examination of most parts of the body including the head.

However the water bag arrangement suffers from the disadvantage that further movement may take place at any time as the bag adjusts to movements of the body. Such movements may occur as a result of, for example, expulsion of blood from surface vessels or, in the case of the head, gradual crushing of the patients hair. If such movements occur in the course of a scan they may result in inaccuracies and interference in the finally calculated reconstruction.

It is an object of this invention to provide a body locating arrangement for which the above disadvantage is reduced.

According to the invention there is provided radiographic apparatus for examining part of the interior of a body by means of penetrating radiation including a packing member comprising a bag containing particulate or viscous material, having an absorption to the radiation similar to that of human tissue, the member as a whole being flexible and being adapted to be placed in contact with said body in the vicinity of the part to be examined, locating means, arranged to maintain said member in place, and means for disposing said locating means in a predetermined position with respect to the source of said radiation.

In order that the invention may be clearly understood and readily carried into effect an example thereof will now be described with reference to the accompanying drawings of which:

Figure 1:
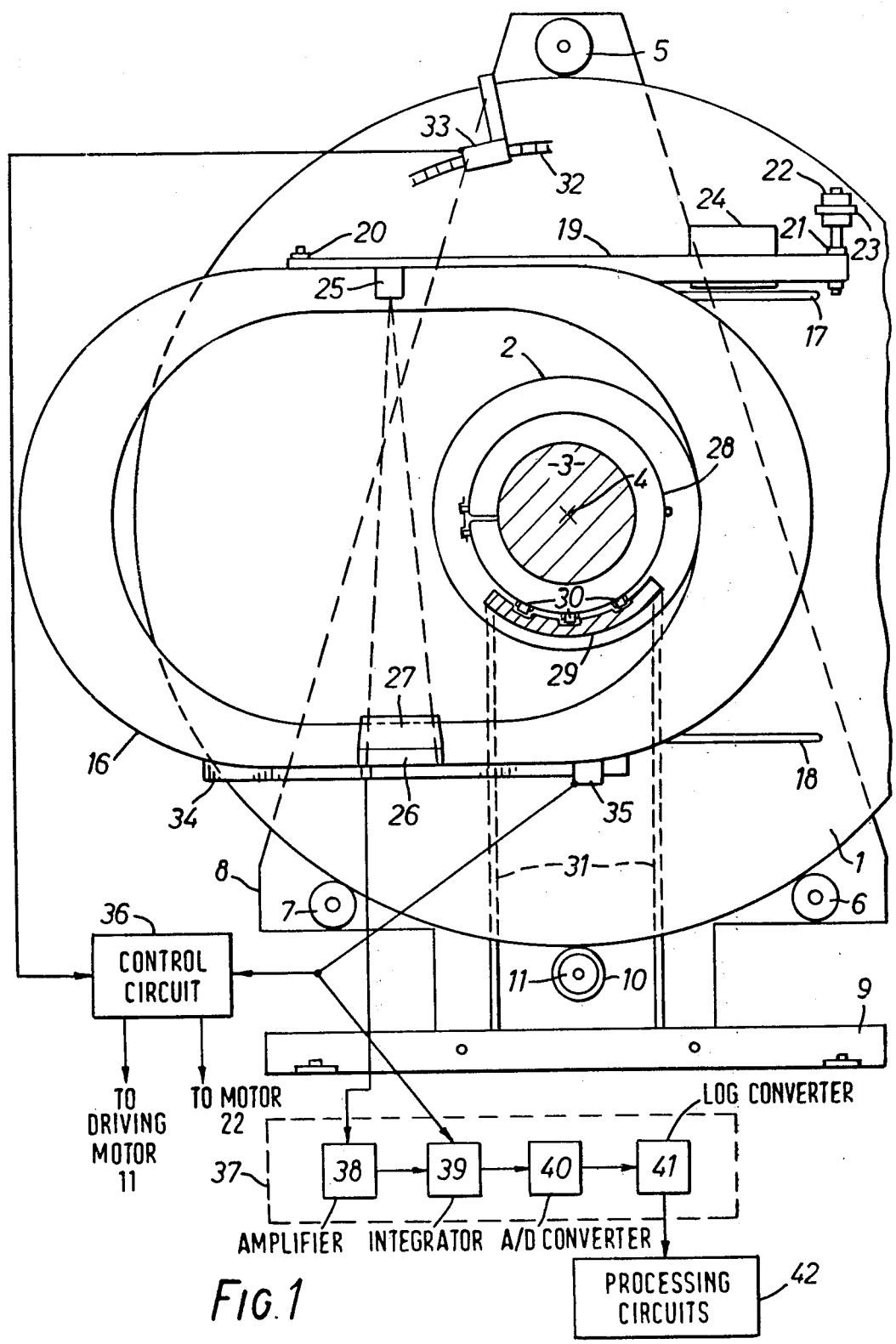
FIG. 1 shows an X-ray apparatus incorporating the invention.

Turning now to FIG. 1, the apparatus shown therein is, in principle, and except in respect of the arrangements for positioning the patient of the type described U.S. Pat. No. 3,946,234 which is a further variation of the apparatus described in the said British Patent.

A turntable member 1, having a central aperture 2, to accommodate the body 3 of a patient to be examined, is mounted vertically for rotation about an axis 4. Axis 4 is disposed centrally in the aperture 2. The member 1 is supported on three rotatable bearings 5, 6 and 7 which are journalled in the main frame 8 of the apparatus. The frame 8 remains stationary, being rigidly secured to a pedestal 9, and can take any suitable form, although it must, of course, be formed with an aperture coincident with the aperture 2.

The member 1 can be rotated in angular steps, in this example by means of a cog wheel 10, cooperating with gear teeth, not shown, cut into the periphery of member 1. Cog wheel 10 is driven by a motor 11 which is fixed to the main frame 8. If desired the gear teeth may take the form of slots so that the arrangement takes the form of a so-called "Geneva mechanism" with cog wheel 10 being replaced by a rotating peg such as is used with that mechanism.

Mounted on the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed as chords thereof. The lateral scanning motion is imparted to the yoke 16 by virtue of a toothed belt 19, which is stretched between a pair of toothed rollers 20 and 21 journalled in respective brackets, not shown, secured to the member 1, and to which belt the yoke 16 is attached by means of a bracket, not shown. The roller 20 is merely an idler roller, but roller 21 is driven by a reciprocating motor 22 which is attached by a strap like bracket 23 to the member 1.

A counterbalance weight 24 is secured to belt 19 on the opposite run to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped spread of radiation, emanating from a substantially point source. On the opposite side of yoke 16, with respect to the aperture 2, to the source 25 is an array 26 of thirty detectors sensitive to the radiation generated by the source 25, each viewing the source through a respective collimator; the collimators being disposed in a bank 27. In this example neighbouring collimators are inclined to each other at an angle of $\frac{1}{3}°$ and, since there are thirty detectors, this means that the angular spread of the beam of X-rays generated by the source is $9\frac{2}{3}°$.

The body 3 is held by a supporting member 28, which will be described in greater detail hereinafter. Member 28 is itself mounted on a support 29 which holds it in a fixed position in directions perpendicular to axis 4 but allows motion in the direction of that axis. In this example this is arranged by having bearings 30 on member 28 run in corresponding tracks on support 29. Means, not shown, are provided to hold member 28 fixed in a desired position along axis 4 during an X-ray scan. Support 29 has also legs 31 which stand on pedestal 9. Member 28 may be removed from support 29 so that it can be changed in size and if desired the patient may be inserted therein before it is refixed. Alternatively member 28 may be moved along axis 4 by means of rollers 30 so that the patient may be inserted. The patient is supported on one or both sides of member 28 by beds or other means, not shown, as necessary. In FIG. 1 an example of member 28 suitable for holding a patients abdomen is shown. That member may also be provided in other sizes suitable for examining other parts of the body, such as the head. The member 28, as described hereinafter, may also be used in conjunction with an X-ray apparatus designed for examining only the head and having a smaller aperture 2. Such apparatus may take essentially the same form as that described but usually employ a smaller number of detectors.

It will be evident that the stepped, rotational scanning motion imparted, by intermittent operation of motor 11, to the member 1 needs to be synchronised with the lateral scanning motion imparted to the yoke 16 by the reciprocating motor 22. To this end the member 1 is formed with an annular graticule part of which is shown at 32, and a fixed photodetector 33 mounted on main frame 8 is provided, together with a suitable light source, not shown, to provide timing pulses indicative of the passage of markings on the graticule 32 past the photodetector 33. Thus the rotational scanning motion of member 1 can be monitored. Similarly a linear graticule 34 is fixedly attached to the yoke 16 and cooperates with a second photodetector 35, which is mounted on the member 1 so as to rotate therewith, and a similarly mounted light source, not shown, to provide timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor 11 in such a way that after each step of rotational motion a single lateral scan is carried out to scan the source 25 and the detector array 26 in one direction or the other across the aperture 2. Thus a single lateral scan is carried out for each dwell angle of the member 1; these dwell angles being, in this example, 10° apart.

Each detector in the array 26 comprises, for example, a scintillator crystal, such as Sodium iodide, and an associated photomultiplier tube, or a photodiode, and thus provides electrical signals indicative of the amount of radiation detected thereby. The electrical signals so provided are applied to respective preprocessing circuits 37, each of which contains an amplifier 38, a resettable integrator 39, an analogue-to-digital converter circuit 40 and a logarithmic converter circuit 41. The integrators 39 are read and reset synchronously and periodically by means of timing pulses derived from the photodetector 35; the arrangement being such that the reading and resetting occurs some four hundred and eighty times during each lateral scan in either direction. Thus, during a single lateral scan, output signals are provided which are indicative of the absorption suffered by the X-radiation on traversing a set of four hundred and eighty parallel paths from the source to the detector at each of thirty angular orientations with respect to the body 3. The member 1 is then rotated through ten degrees and a second group of 30 sets of four hundred and eighty output signals are derived. The process is repeated until the member 1 has been rotated through, say, 170° and all of the output signals obtained during the scanning are processed in a processing circuit 42 to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described and claimed in our U.S. Pat. No. 3,924,129. This technique involves a form of convolution and the output signals are assembled in sets relating to parallel paths through the body. Each output is then modified by combining it with weighted components of other output signals of its own sets; the weighting being in accordance with a function which is negative, and decreasing in amplitude as the distance, from the path giving rise to the output signal being weighted to the path giving rise to the output signal being modified, increases. The modified output signals are then additively combined in accordance with a layergramming procedure; the modification of the output signals being such as to compensate for the known inaccuracies of conventional layergrams.

Returning to the manner of positioning the body 3, the construction of member 28 will now be considered in greater detail. As mentioned hereinbefore, the waterbag, which can be used for positioning and equalising of X-ray absorption, allows movement of the body to an extent which may be undesirable. This invention therefore provides an alternative material which may be thick and viscous with a consistency similar to that of dough or else polystyrene grains, mixed with polyvinylacetate (PVA) powder to give a suitable consistency. The material also, of course, has an X-ray absorption similar to that of body tissue. This material may be used to fill bags, similar to the water bags discussed hereinbefore, which are wrapped around the body 3 before it is enclosed in a two part retaining ring such as that disclosed in U.S. Pat. No. 3,937,963. The material may also be provided in the form of packs of various sizes which can be used to fill spaces around the body, such as at the sides and under the back, to give an approximately circular cross-section to the radiation. In that case the body need only be supported on a simple, preferably slightly dished, bed or support and restrained reasonably firmly by means such as a strap.

Figure 2:
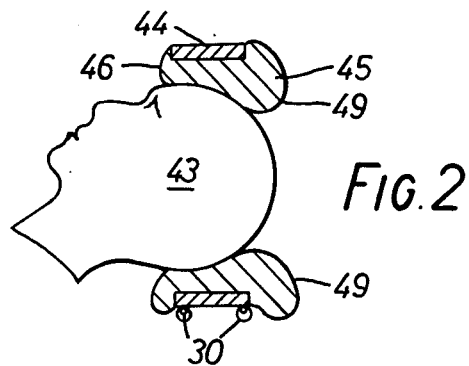
FIG. 2 shows an arrangement of a retaining member, suitable for use with the invention, in place about a head

In this example of the invention, however, the material is provided integrally with the member 28 which holds the body 3 in position. In FIG. 2 there is shown an example of a member 28 which is suitable for holding a head denoted by reference 43. It will be apparent that the only differences between the example shown in FIG. 2 and an example for holding other parts of a body are one of scale and minor differences which may prove convenient in practice.

The outer part of member 28 is a locating ring 44 which is essentially the same as that described in the said U.S. Pat. No. 3,937,963. In the space between ring 44 and the patients head 43 there is disposed the dough-like material 45 previously mentioned. This material is contained in a close-fitting flexible bag 46, such as a rubber bag, which is, in this example, fixed to the outside of the ring 44. Ring 44 is shown of exaggerated thickness to make the fitting more clear. All air is extracted from the rubber bag, after filling it with the material 45, by evacuating and sealing the bag. FIG. 2 also shows the bearings 30 which are placed so as not to interfere with X-rays in any plane of examination. These bearings may, of course, be replaced with other fixing or locating means as desired.

Figure 3A:
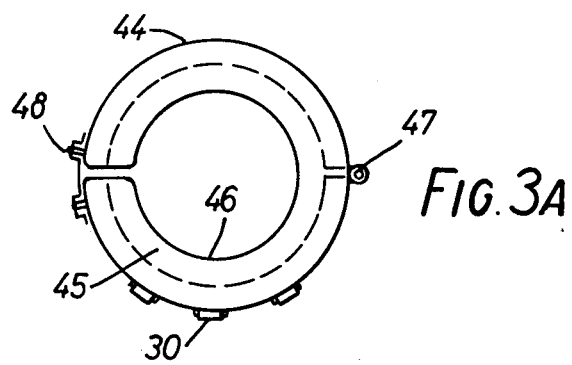
FIG. 3a and 3b show the member of FIG. 2 in closed and open positions respectively.
Figure 3B:
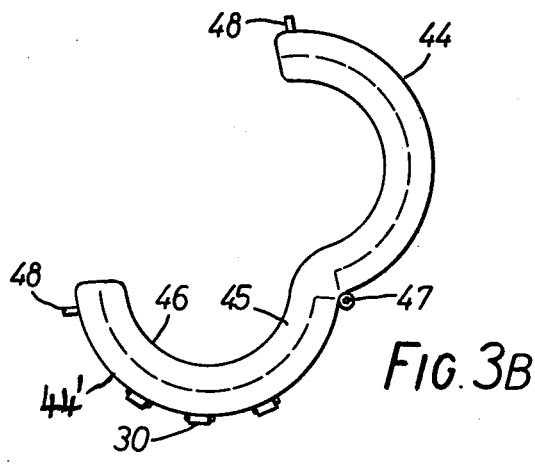

The ring, without head 43 is also shown in end elevation in FIGS. 3a and 3b, in closed and open positions respectively. Reference numerals 30, 44, 45 and 46 have the significance explained hereinbefore. The inner surface of ring 44 is here shown by the broken line since it is in this example inside bag 46 and therefore not visible. It can be seen in FIG. 3 that the ring 44 is in two parts joined at one side by a hinge 47 and closed at the other side at position 48 by a clip, clamp or other suitable means.

In use the patient's head is placed in the two halves of the ring, open as in FIG. 3b with bag 46 arranged so that most of the material 45 is inside ring 44. The viscosity of the material 45 is chosen so that it will remain in any position in which it is placed without interference but will move readily in response to firm pressure. The ring halves are then closed to attain the position of FIGS. 2 and 3a. The closure is carried out carefully so that the material is allowed to flow from between the head and the ring. The flexibility of bag 46 allows the material to be extruded from the inside of the ring as shown at points 49 in FIG. 2. Care should be taken that no air pockets remain between the head and the bag 46, that the movement of closing is not too fast, so as to cause discomfort to the patient, and that the extruded material does not flow over the patients eyes if these are close to the ring.

By this means it is possible to ensure that the space between ring 44 and the head 43 is filled entirely with material 45 for many different sizes of head. To encompass a large variety of such head sizes, however, alternative sizes of ring 44 are employed.

It will be appreciated that the bag 46 need not be attached to the ring 44 if this is not required.

Furthermore, if patient movement does not provide excessive problems only the lower half (44') of ring 44 need be provided to give support for the body as mentioned hereinbefore. In that case it may be less than semicircular but should be fitted with bag 46 or loose bags of the viscous or particulate material as described hereinbefore.

As explained hereinbefore, the material 45 is chosen to have a viscosity such that it will move readily but only in response to positive action. It must also have X-ray absorption similar to that of body tissue.

The material used in practice is based on an emulsifying ointment which is available as a standard British Pharmaceutical preparation and is a mixture of emulsifying wax, white soft paraffin and liquid paraffin. This is mixed with about twice its weight of water and a small quantity of chlorocresol, to reduce bacterial activity, to make an aqueous cream.

A small proportion of a long chain cellulosic filler, in this example sodium carboxymethyl cellulose, is then added. This material, which can be described as a cellulosive thickening agent, is varied to provide the required viscosity. Finally a suitable quantity of alpha cellulose, a highly refined and chemically pure sawdust, is added. All mixing may be carried out in a suitable mechanical mixer. Material made as described normally has a suitable absorption coefficient to X-radiation. However, should the absorption of this, or other material, need adjustment it may be altered by the admixture of particles of a strongly X-ray absorbing material.

If a particulate material is to be used a suitable form is polystyrene particles mixed with a polyvinylacetate(PVA) powder, preferably in the proportions of, approximately, two parts of particles to one part of PVA powder by volume.

It will be appreciated that other similar materials may be substituted provided the material obtained has the properties discussed hereinbefore.

The positioning arrangement described may, of course, be used with other forms of apparatus than that described in relation to FIG. 1, for example variation of that apparatus in which the orbital motion is continuous during the lateral scan, or in which only the orbital motion is provided, the lateral scan being omitted.

What I claim is:

1. Radiographic apparatus for examining part of the interior of body by means of penetrating radiation including a packing member comprising a bag containing a mixture of emulsifying ointment with a cellulosic filler, said mixture having an absorption to the radiation similar to that of human tissue, the member as a whole being flexible and being adapted to be placed in contact with said body in the vicinity of the part to be examined, locating means, arranged to maintain said member in place, and means for disposing said locating means in a predetermined position with respect to the source of said radiation.

2. An apparatus according to claim 1 in which the cellulosic filler is sodium carboxymethyl cellulose.

3. An apparatus according to claim 1 in which the emulsifying ointment is a mixture of emulsifying wax, white soft paraffin and liquid paraffin.

4. An apparatus according to claim 1 in which the said mixture further includes a proportion of alpha cellulose.

5. An apparatus according to claim 1 in which the said mixture further includes particulate material, which is strongly absorbing of X-radiation, for the purpose of adjusting its absorption coefficient.

6. Radiographic apparatus for examining part of the interior of a body by means of penetrating radiation including a packing member comprising a bag containing a mixture of polystyrene particles with a polyvinylacetate powder, said mixture having an absorption to the radiation similar to that of human tissue, the member as a whole being flexible and being adapted to be placed in contact with said body in the vicinity of the part to be examined, locating means, arranged to maintain said member in place, and means for disposing said locating means in a predetermined position with respect to the source of said radiation.

7. An apparatus according to claim 6 in which said locating means is a single curved member arranged to support the body.

8. An apparatus according to claim 6 in which the proportion of polystyrene particles to polyvinylacetate powder is approximately 2 to 1 by volume.

9. An apparatus according to claim 6 in which said material contains particulate material, which is strongly absorbing of X-radiation, for the purpose of adjusting its absorption coefficient.

10. Radiographic apparatus comprising:
means defining a patient position and means disposed outside the patient position for generating penetrating radiation and projecting it through the patient position to emerge therefrom after suffering absorption determined by matter through which it has travelled;
means for detecting the radiation emerging from the patient position and measuring its intensity to derive therefrom a representation of the variation of absorption of the radiation in matter disposed in the patient position;
positioning means for disposing a part of the body of the patient within the patient position, the positioning means comprising a packing member in the form of a bag containing a mixture of alpha cellulose with another material, the mixture having an absorption to the radiation similar to that of human tissue, the member as a whole being flexible and being adapted to be placed in contact with the body in the vicinity of said part, locating means, arranged to maintain said member in place, and means for disposing the locating means in a predetermined disposition in the patient position.

* * * * *